United States Patent [19]

Shaffer et al.

[11] Patent Number: 4,856,505
[45] Date of Patent: Aug. 15, 1989

[54] APPARATUS FOR RELIEVING PAIN AND DISCOMFORT OF A BUNION

[76] Inventors: David E. Shaffer, 386 Spruce La., East Meadow, N.Y. 11554; Michael P. Della Corte, 283 Carnation Ave., Floral Park, N.Y. 11001

[21] Appl. No.: 228,471

[22] Filed: Aug. 5, 1988

[51] Int. Cl.⁴ ............................................. A61F 13/00
[52] U.S. Cl. .................................. 128/81 R; 128/157
[58] Field of Search .................. 128/94, 95, 96, 81 R, 128/800, 157, 581, 595, 596, 608; 2/22

[56] References Cited

U.S. PATENT DOCUMENTS 3,049,120  9/1959  Marcus ............................. 128/81 R
4,745,927  5/1988  Brock ........................... 128/81 R X Primary Examiner—Richard J. Apley
Assistant Examiner—Natalie Paul
Attorney, Agent, or Firm—Michael I. Kroll

[57] ABSTRACT

An apparatus for relieving pain and discomfort of a bunion is provided and consists of a mitten-like sock with a restraining member for the big toe. The sock is worn on the foot so that the big toe is physically pulled back to a somewhat normal position with respect to the other toes of the foot thus relieving pain and discomfort to the bunion.

1 Claim, 1 Drawing Sheet

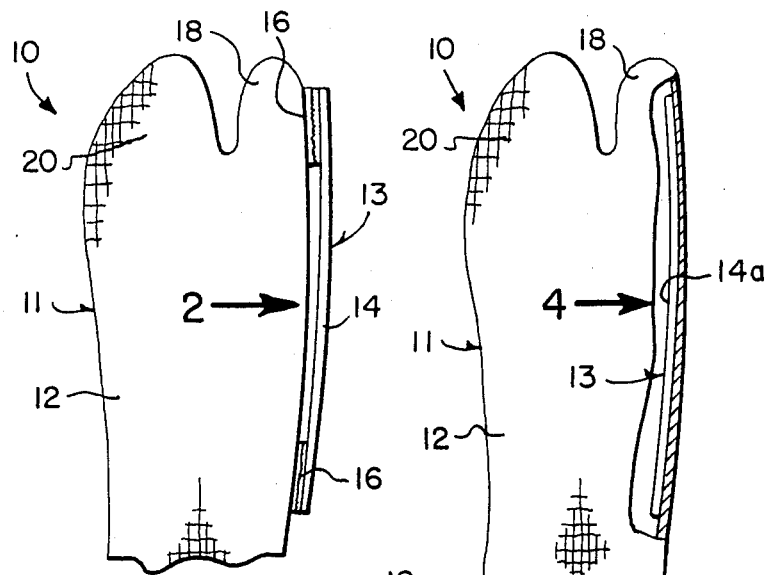
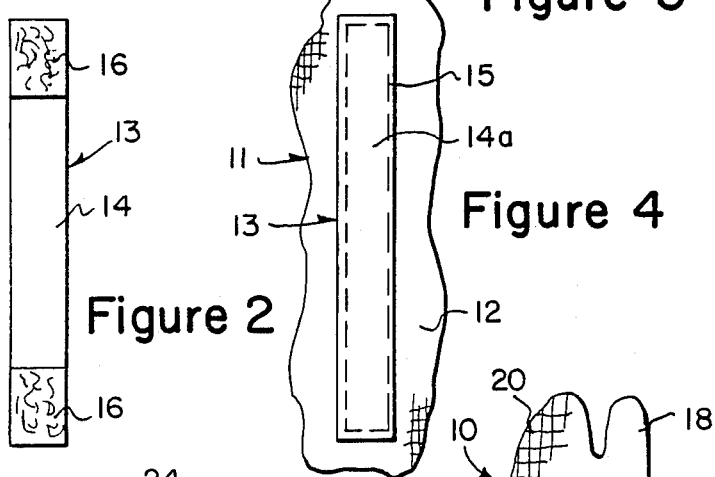
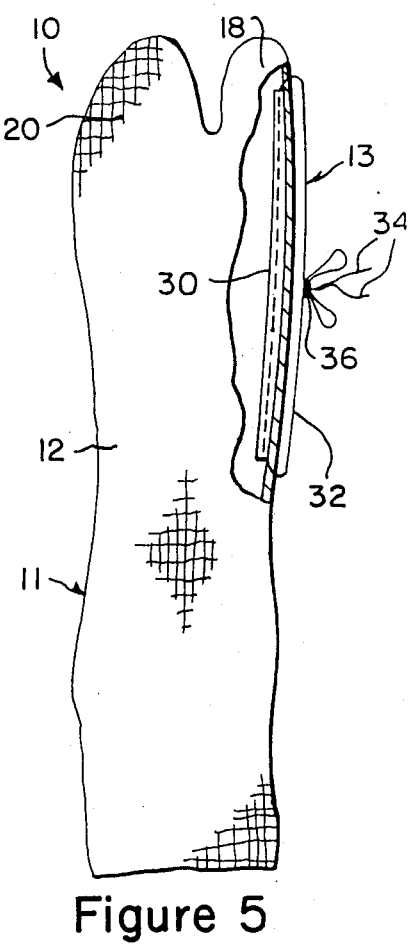
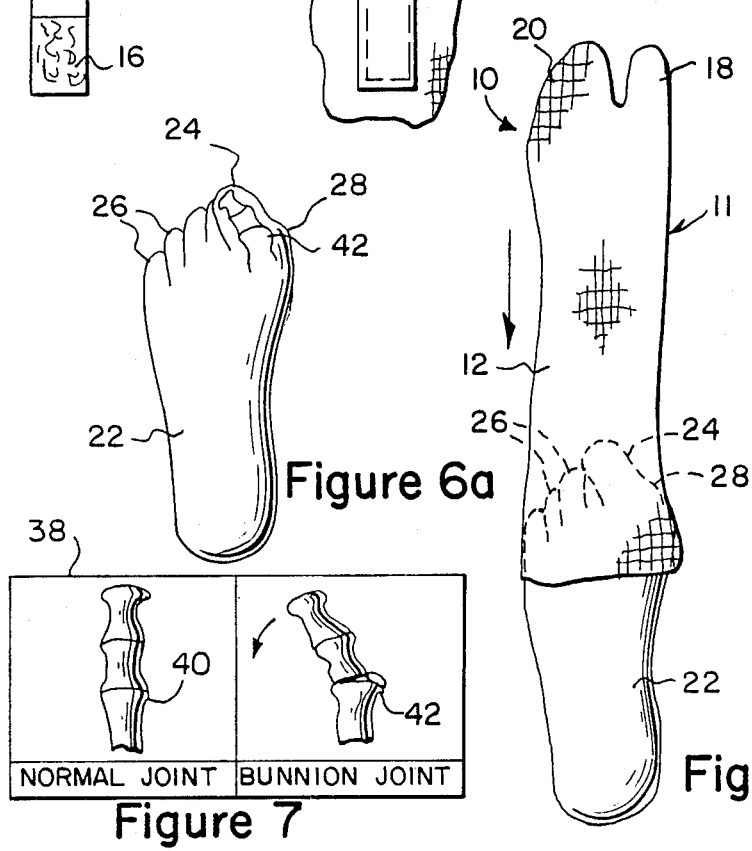
Figure 1
Figure 2
Figure 3
Figure 4
Figure 5
Figure 6a
Figure 6b
Figure 6c
Figure 7
NORMAL JOINT | BUNNION JOINT

APPARATUS FOR RELIEVING PAIN AND DISCOMFORT OF A BUNION

BACKGROUND OF THE INVENTION

1. Field of the Invention

The instant invention relates generally to corrective footwear and more specifically it relates to an apparatus for relieving pain and discomfort of a bunion.

A bunion is the inflammation and thickening of the bursa of the joint of the great toe, usually associated with marked enlargement of the joint and displacement of the toe laterally. The bursa is a padlike sac or cavity found in connecting tissue usually in the vicinity of joints. It is lined with synovial membrane and contains a fluid, synovia, which acts to reduce friction. Properly fitting shoes and support of the metatarsal arch usually relieves pain and discomfort, but in severe cases operative correction of the deformity is required.

2. Description of the Prior Art

Numerous corrective footwear have been provided in prior art that are adapted to relieve various deformities of the feet. While these units may be suitable for the particular purpose to which they address, they would not be as suitable for the purposes of the present invention as heretofore described.

SUMMARY OF THE INVENTION

A primary object of the present invention is to provide an apparatus for relieving pain and discomfort of a bunion that will overcome the shortcomings of the prior art devices.

Another object is to provide an apparatus for relieving pain and discomfort of a bunion that is a mitten-like sock with a restraining member worn on the foot to physically pull the big toe back to a somewhat normal position with respect to the other toes of the foot.

An additional object is to provide an apparatus for relieving pain and discomfort of a bunion that will retard further growth of the bunion.

A further object is to provide an apparatus for relieving pain and discomfort of a bunion that is simple and easy to use.

A still further object is to provide an apparatus for relieving pain and discomfort of a bunion that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific constrction illustrated and described within the scope of the appended claims.

BRIEF DESCRIPTION OF THE DRAWING FIGURES

FIG. 1 is a top view with parts broken away of a first form of the invention.

FIG. 2 is a view taken in direction of arrow 2 in FIG. 1 showing the detachable restraining member in greater detail.

FIG. 3 is a top view with parts broken away of a second form of the invention.

FIG. 4 is a view taken in direction of arrow 4 in FIG. 3 showing the built-in restraining member in greater detail.

FIG. 5 is a top view with parts broken away of a third form of the invention.

FIG. 6a is a top view of the bunion foot alone.

FIG. 6b is a top view of the invention being placed onto the bunion foot.

FIG. 6c is a top view of the invention on the bunion foot showing the big toe pulled away from the small toes.

FIG. 7 is a chart showing a normal joint and a bunion joint of the big toe.

DETAILED DESCRIPTION OF THE PREFERRED EMBODIMENTS

Turning now descriptively to the drawings, in which similar reference characters denote similar elements throughout the several views, FIGS. 1 through 5 generally illustrate an apparatus 10 for relieving pain and discomfort to a bunion 28 on a big toe 24 of a foot 22. The apparatus 10 consists of a mitten-like sock 11 having a body portion 12, a big toe portion 18 and a small toes portion 20. As shown in FIG. 6c, the sock 11 is worn on the foot 22 so that the big toe 24 fits into the big toe portion 18 and other small toes 26 fit into the small toes portion 20. A structure 13 is attached to the sock 11 for physically pulling back the big toe 24 to a somewhat normal position with respect to the other toes 26 of the foot 22 thus relieving pain and discomfort to the bunion 28.

As shown in FIGS. 1 and 2, the structure 13 includes an elongated rectangular rigid restraining member 14 and a pair of hook and loop pile fasteners 16. One of the fasteners 16 is attached to outside of the big toe portion 18 and one end of the restraining member 14 while other of the fasteners 16 is attached to outside of the body portion 12 and other end of the restraining member 14 so that the restraining member can be removably attached thereto to physically pull back the big toe 24.

As shown in FIGS. 3 and 4, the structure 13 includes an elongated rectangular rigid restraining member 14a and a plurality of stitches 15 for attaching the restraining member 14a to inside of the big toe portion 18 and inside of the body portion 12 so that the restraining member 14a is permanently attached thereto to physically pull back the big toe 24.

As shown in FIG. 5, the structure 13 includes an elongated sleeve 30 affixed to inside of the big toe portion 18 and inside of body pojtion 12 so that the sleeve 30 is permanently attached thereto. A draw string 32 fits through the sleeve 30 with ends 34 extending out of the sock 11 and tied together, at 36, to physically pull back the big toe 24.

FIG. 6a shows the foot 22 with bunion 28 before insertion of the sock 11, FIG. 6b shows the sock 11 being inserted on the foot 22 and FIG. 6c shows the sock 11 completely in place with the big toe 24 pulled back.

FIG. 7 shows a chart 38 with a normal joint 40 compared to a bunion joint 42. When the invention 10 is worn on the foot 22 the big toe 24 will be in a somewhat normal position relieving pain and discomfort to the bunion joint 42 within the bunion 28.

Small toe portion 20 as a group may likewise be restrained (not shown) and as an alternate configuration each toe may have its own pocket similar to big toe portion 18 so that each toe may be selectively restrained(not shown).

LIST OF REFERENCE NUMBERS 10 apparatus
11 mitten-like sock
12 body portion
13 structure
14 restraining member
14a restraining member
15 stitches
16 hook and loop pile fastener
18 big toe portion
20 small toes portion
22 foot
24 big toe
26 small toes
28 bunion joint
30 sleeve
32 draw string
34 end
36 tie
38 chart
40 normal joint
42 bunion joint It will be understood that each of the elements described above, or two or more together, may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An apparatus worn within a shoe for relieving pain and discomfort to a bunion on a big toe of a foot having an ankle, said apparatus comprising:
   (a) a one size fits all mitten-like sock enclosing the entire foot up to the ankle and having a body portion, a big toe portion and a small toes portion, said sock worn on the foot so that the big toe fits into said big toe portion and other small toes fit into said small toes portion, said sock being reversible making said sock useable on the right and left foot with minimal adjustment; and
   (b) means attached externally to said sock for physically realigning the big toe to a normal position so that the big toe is properly positioned to promote mobility and stability while the device is worn and thus relieving pain and discomfort from the bunion, said pulling back means running longitudinally in the direction of the length of the foot and including an elongated rectangular rigid restraining member and a pair of hook and loop pile fasteners, one of said fasteners attached to outside of said big toe portion and one end of said restraining member while other of said fasteners attached to outside of said body portion near the waist portion and other end of said restraining member so that said restraining member can be removably attached thereto to physically realign the big toe, said pair of hook and loop pile fasteners providing adjustability for different sized feet.

* * * * *